United States Patent
Turco

(10) Patent No.: US 11,117,957 B2
(45) Date of Patent: Sep. 14, 2021

(54) ANTI-BAG3 ANTIBODIES FOR THERAPEUTIC USE

(71) Applicant: BIOUNIVERSA S.R.L., Fisciano (IT)

(72) Inventor: Maria Caterina Turco, Avellino (IT)

(73) Assignee: BIOUNIVERSA S.R.L., Montoro (IT)

(*) Notice: Subject to any disclaimer, the term of this patent is extended or adjusted under 35 U.S.C. 154(b) by 247 days.

(21) Appl. No.: 16/141,911

(22) Filed: Sep. 25, 2018

(65) Prior Publication Data

US 2019/0010221 A1 Jan. 10, 2019

Related U.S. Application Data

(63) Continuation of application No. 14/651,213, filed as application No. PCT/IB2014/059416 on Mar. 4, 2014, now abandoned.

(30) Foreign Application Priority Data

Mar. 18, 2012 (IT) .......................... MI2013A000403

(51) Int. Cl.
*C07K 16/18* (2006.01)
*C07K 16/30* (2006.01)
*A61K 39/00* (2006.01)

(52) U.S. Cl.
CPC ............ *C07K 16/18* (2013.01); *C07K 16/303* (2013.01); *A61K 2039/505* (2013.01); *A61K 2039/54* (2013.01); *C07K 2317/14* (2013.01); *C07K 2317/73* (2013.01); *C07K 2317/76* (2013.01)

(58) Field of Classification Search
CPC .. C07K 16/18; C07K 16/303; C07K 2317/14; C07K 2317/76; C07K 2317/73; A61K 2039/54; A61K 2039/505; A61P 37/02; A61P 35/00; A61P 29/00; A61P 25/28
See application file for complete search history.

(56) References Cited

U.S. PATENT DOCUMENTS

2005/0176660 A1 8/2005 Leone et al.

FOREIGN PATENT DOCUMENTS

| WO | 2000/014106 A1 | 6/2000 |
| WO | 2003/055908 A2 | 7/2003 |
| WO | 2009/014759 A2 | 1/2009 |
| WO | 2011/067377 A1 | 6/2011 |
| WO | 2013/189775 A1 | 12/2013 |

OTHER PUBLICATIONS

Product, MABC282 Sigma-Aldrich Anti-BAG3 Antibody, clone AC-1clone AC-1, from mouse, printed Aug. 17, 2020.*

Liao et al. The anti-apoptotic protein BAG-3 is overexpressed in pancreatic cancer and induced by heat stress in pancreatic cancer cell lines. FEBS Letters 503 (2001) 151-157.*

Keah, Hooi Hong et al., "Direct synthesis and characterisation of multi-dendritic peptides for use as immunogens", Journal of Peptide Research, 1998, vol. 51, pp. 2-8.

Rosati, A. et al., "BAG3: a multifaceted protein that regulates major cell pathways", Cell Death and Disease, 2011, 2(4): e141, 6 pages.

Ammirante, Massimo et al., "IKKγ protein is a target of BAG3 regulatory activity in human tumor growth", Proceedings of the National Academy of Sciences, Apr. 2010, vol. 107, No. 16, pp. 7497-7502.

Ceran, Ceyhan et al., "Novel anti-HER2 monoclonal antibodies: synergy and antagonism with tumor necrosis factor-α", BMC Cancer, 2012,12:450, 16 pages.

Franceschelli, Silvia et al., "bag3 Gene Expression Is Regulated by Heat Shock Factor 1", Journal of Cellular Physiology, 2008, pp. 575-577.

Ota, Seisuke et al., "Cellular Processing of a Multibranched Lysine Core with Tumor Antigen Peptides and Presentation of Peptide Epitopes Recognized by Cytotoxic T Lymphocytes on Antigen-presenting Cells'", Cancer Research, Mar. 2002, vol. 62, pp. 1471-1476.

Tam, James P. "Synthetic peptide vaccine design: Synthesis and properties of a high-density multiple antigenic peptide system", Proceedings of the National Academy of Sciences, Aug. 1988, vol. 85, pp. 5409-5413.

Tassone, P. et al., "CD36 is rapidly and transiently upregulated on phytohemagglutinin (PHA)-stimulated peripheral blood lymphocytes. Analysis by a new monoclonal antibody (UN7)." Tissue Antigens. Jun. 1998; 51(6):671-5 (abstract only).

Festa, Michelina et al., "BAG3 Protein Is Overexpressed in Human Glioblastoma and Is a Potential Target for Therapy", The American Journal of Pathology, Jun. 2011, vol. 178, No. 6, pp. 2504-2512.

Falco, Antonio, "PhD thesis in Role of protein in the tumor microenvironment BAG3", Department of pharmaceutical sciences and biomedical, 2011, Retrieved from Internet: URL:http://elea.unisa.it/jspui/bitstream/10556/293/1/tesi%20%20A.%20Falco.pdf [retrieved Oct. 14, 2013].

Rosati, Alessandra et al., "Expression of the Antiapoptotic Protein BAG3 Is a Feature of Pancreatic Adenocarcinoma and Its Overexpression Is Associated With Poorer Survival", The American Journal of Pathology, Nov. 2012, vol. 181, No. 5, pp. 1524-1529.

Wang, Hua-Qin et al., "Characterization of BAG3 Cleavage During Apoptosis of Pancreatic Cancer Cells", Journal of Cellular Physiology, Jul. 2010, pp. 94-100.

International Search Report for International Application No. PCT/IB2014/059416, dated Sep. 15, 2014.

Behl, Christian (Trends in Pharmacological Sciences 37(8): 672-688, Aug. 2016).

* cited by examiner

*Primary Examiner* — Alana Harris Dent
(74) *Attorney, Agent, or Firm* — Perkins Coie LLP; Viola T. Kung

(57) ABSTRACT

The present invention relates to the use of BAG3 antibodies as a medicament, in particular for use in the treatment of pancreatic tumours or other pathologies of an immune, inflammatory, neoplastic and/or degenerative nature.

3 Claims, 3 Drawing Sheets
Specification includes a Sequence Listing.

Figure 1. Image of peritoneal spread
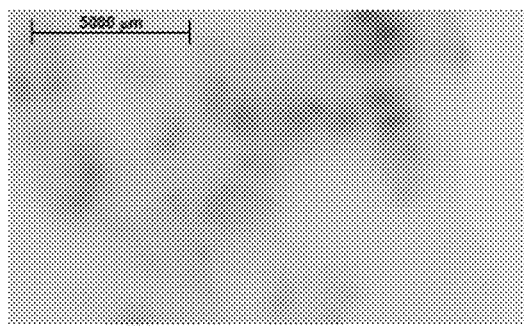 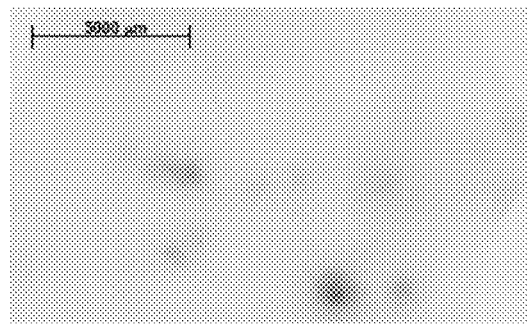
Control IgG					Ac-rb2 anti-Bag3 antibody

ANTI-BAG3 ANTIBODIES FOR THERAPEUTIC USE

This application is a continuation of U.S. application Ser. No. 14/651,213, filed Jun. 10, 2015, which is a National Stage of International Application PCT/IB2014/059416, filed Mar. 4, 2014, published Sep. 25, 2014, under PCT Article 21(2) in English; which claims the priority of Italian Application No. MI2013A000403, filed Mar. 18, 2013. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Jun. 20, 2017, and a size of 5.73 kilobytes. The Sequence Listing filed via EFS-Web is part of the specification and is hereby incorporated in its entirety by reference herein.

DESCRIPTION

The present invention relates to the use of Anti-BAG3 antibodies as a medicament, in particular for use in the treatment of pancreatic tumours or other pathologies of an immune, inflammatory, neoplastic and/or degenerative nature.

STATE OF THE ART

BAG3 protein is a 74 kDa cytoplasmic protein which belongs to the family of co-chaperonins that interact with the ATPase domain of the protein HSP70 (Heat Shock Protein) through the structural domain known as the BAG domain (amino acids 110-124). Furthermore, BAG3 protein contains a WW domain (Trp-Trp), a proline-rich region (PXXP), and two conserved motifs IPV (Ile-Pro-Val), which can mediate binding to other proteins. Thanks to the nature of BAG3 protein as an adapter, attributable to the presence of many functional domains, such protein can therefore interact with different proteins.

In humans, bag3 gene expression is constitutive for a few kinds of normal cells, including myocytes, while mutations thereof are associated with diseases of the skeletal and cardiac muscles. Furthermore, BAG3 protein is expressed in many types of primary tumours or tumour cell lines (lymphoid or myeloid leukemias, neuroblastoma, pancreatic cancer, thyroid cancer, breast cancer and prostate cancer, melanoma, osteosarcoma, glioblastoma and tumours of the kidney, colon, and ovary).

In normal cell types, such as leukocytes, epithelial cells and glial cells and cells of the retina, bag3 gene expression can be induced by stressors, such as oxidants, high temperatures, lack of serum, heavy metals, HIV-1 infections, etc. These findings indicate that bag3 gene expression regulation is an important component in the cellular response to stress and is correlated with the presence of elements that respond to the transcription factor HSF1 (Heat Shock Transcription Factor), which is activated in various forms of cellular stress in bag3 gene promoter (Franceschelli S., et al. J Cell Physiol 215 (2008) 575-577).

Moreover, due to the presence of many protein-protein interaction domains in the structure thereof, BAG3 protein influences cell survival in different types of cells, interacting with different molecular partners. (A. Rosati et al. Cell Death Dis. (2011) 2:e141). The first mechanism reported in relation to BAG3 anti-apoptotic activity was identified in osteosarcoma and melanoma cells, where it was observed that BAG3 protein modulates the activation of transcription factor NF-kB and cell survival (Ammirante M. et al., Proc Natl Acad Sci USA 107 (2010) 7497-7502). A different molecular mechanism has been described in glioblastoma cells, where BAG3 protein cooperates in a positive way with HSP70 protein to maintain BAX protein in the cytosol and prevent the translocation thereof into the mitochondria (Festa M. et al., Am J Pathol 178 (2011) 2504-25). Finally, in some tumours, BAG3 has been shown to regulate proteins that modulate cell adhesion.

The presence of cytoplasmic BAG3 protein has also been described in many different cellular systems and has been associated, not only with various tumours, but also in pathologies in general related to cell survival.

Furthermore, patent application WO2011/067377 describes soluble BAG3 protein, secreted externally to the cell, as a biochemical marker in serum, which is highly specific for the diagnosis of certain pathological conditions, such as cardiac pathologies and pancreatic tumour. In particular, it has been demonstrated that, in patients suffering from pancreatic adenocarcinoma, the concentration of (extra-cellular) soluble BAG3 is generally greater than 10 ng/ml.

Furthermore, it has recently been reported that BAG3 protein is expressed in 346/346 patients with pancreatic ductal adenocarcinoma (PDAC) and is released by the cells of the pancreatic tumour, but such protein is not expressed in either the surrounding non-neoplastic tissues or in a normal pancreas; likewise, it has been reported that the levels of BAG3 expression are related to patient survival. The results of the study demonstrate that the use of specific siRNA molecules for BAG3 mRNA can silence bag3 gene expression and induce cell death, confirming that BAG3 protein is an important survival factor for pancreatic tumour cells and that the down-regulation thereof, when combined with gentamicin, may contribute to the eradication of the tumor cells (Rosati et al., Am J Pathol. 2012 November; 181 (5):1524-9).

As it is known, conventional chemotherapy treatments for tumour pathologies, as well as treatments of inflammatory and immune diseases with corticosteroids or NSAIDs (non-steroidal anti-inflammatory drugs) pose numerous drawbacks linked to side effects and are not, at present, definitive means of treating such pathologies.

There is therefore an evident need for a new and improved therapeutic treatment which has the advantage of being highly specific and having few or no side effects, as compared with the conventional, commonly known therapies used for the treatment of diseases of an inflammatory, immune, and neoplastic nature described in the present invention.

DESCRIPTION OF THE INVENTION

Surprisingly, it has been demonstrated, for the first time, that the inhibition of soluble (i.e. extra-cellular) BAG3 protein through the use of anti-BAG3 monoclonal antibodies, impairs development of pancreatic tumour cells. Anti-BAG3 antibodies represent a new and improved therapeutic tool for the treatment of pancreatic tumours. Furthermore, it has also been found, surprisingly, that the aforesaid BAG3 protein is involved in the activation of macrophages.

Therefore, treatment with any of the anti-BAG3 antibodies described in patent application no. WO03/055908 able to inhibit, specifically, the activity of soluble BAG3 protein (i.e. extra-cellular) on macrophages, that are considered the target cells, proves particularly effective in the treatment of those pathologies characterised by the activation of macrophages, such as neoplastic diseases and diseases of an inflammatory, immune, or degenerative nature. In fact, these specific antibodies for BAG3 can bind and block, in a highly selective and targeted manner, pathological effects related to BAG3 protein when secreted by cells.

In particular, the use of anti-BAG3 antibodies in this process has the surprising advantage of being more specific for the selected pathological states characterised by the over-expression and release of BAG3 protein, and also less damaging in terms of side effects.

The term "soluble BAG3 protein" is understood as extra-cellular BAG3 protein, i.e. the protein secreted externally to the cell.

One aim of the present invention is therefore the use of anti-BAG3 antibodies as a medicament.

The antibodies useable in accordance with the present invention may be either monoclonal or polyclonal antibodies, and preferably monoclonal antibodies.

Still more preferably, said monoclonal antibodies may be chosen from the following: murine antibodies, humanized antibodies, chimeric antibodies, recombinant antibodies, conjugated antibodies, scFv fragments (diabody, triabody and tetrabody), Fab fragments, and fragments F(ab')$_2$.

The term "polyclonal antibody" refers to a mixture of antibodies which are genetically different since produced by different plasma cells and which recognise a different epitope of the same antigen.

The term "monoclonal antibody" refers to a set of antibodies which are all identical since produced by cell lines from only one type of immune cell (i.e. a cell clone).

The term "humanized antibody" refers to an antibody of human origin, whose hypervariable region has been replaced by the homologous region of non-human monoclonal antibodies.

The term "chimeric antibody" refers to an antibody containing portions derived from different antibodies.

The term "recombinant antibody" refers to an antibody obtained using recombinant DNA methods.

The term "conjugated antibody" refers to antibodies conjugated with drugs, toxins, radioactive substances or other agents.

The term "scFv fragment" (single chain variable fragment) refers to immunoglobulin fragments only capable of binding with the antigen concerned. ScFv fragments can also be synthesised into dimers (diabodies), trimers (triabodies) and tetramers (tetrabodies) using peptide linkers.

The terms "Fab fragment" (antigen-binding fragment) and "Fab2 fragment" refer to immunoglobulin fragments consisting of a light chain linked to the Fc fragment of the adjacent heavy chain, and such fragments are monovalent antibodies. When the Fab portions are in pairs, the fragment is called Fab2.

The term "hybridoma" refers to a cell producing monoclonal antibodies.

The monoclonal antibodies used in the examples were obtained by immunising mice against four distinct BAG3 protein peptides using any method known to a person skilled in the art. Such peptides were chosen because they are BAG3 protein-specific and are not shared with any other protein, including BAG proteins.

The sequences of the four peptides are included in the BAG3 amino acid sequence (RefSeq: NP_004272; Gene ID 9531, SEQ ID NO: 5) and are selected from the following:
SEQ ID NO 1: DRDPLPPGWEIKIDPQ; (includes BAG3 protein amino acids 18-33);
SEQ ID NO 2: SSPKSVATEERAAPS; (includes BAG3 protein amino acids 385-399);
SEQ ID NO 3: DKGKKNAGNAEDPHT; (includes BAG3 protein amino acids 533-547);
SEQ ID NO 4: NPSSMTDTPGNPAAP; (includes BAG3 protein amino acids 561-575).

Preferably, said antibodies may be obtained by means of the Multiple Antigen Peptide approach (MAP) (Keah H H et al., J Pept Res (1988); 51: 2. Tam J P; Proc Natl acad Sci USA (1988), 85: 5409. Ota S, et al., Cancer Res (2002), 62: 1471), using the following map constructs:
MAP-BAG3-1: nh2-DRDPLPPGWEIKIDPQ-MAP (which contains sequence SEQ ID NO: 1);
MAP-BAG3-2: nh2-SSPKSVATEERAAPS-MAP (which contains sequence SEQ ID NO: 2);
MAP-BAG3-3: nh2-DKGKKNAGNAEDPHT-MAP (which contains sequence SEQ ID NO: 3);
MAP-BAG3-4: nh2-NPSSMTDTPGNPAAP-MAP (which contains sequence SEQ ID NO: 4);

According to a preferred embodiment of the present invention, said polyclonal anti-BAG3 antibodies are obtained by immunising the animals against one of the four peptides of the sequences SEQ ID NO. 1-4 stated above.

According to a preferred embodiment, the monoclonal anti-BAG3 antibodies of the present invention are obtained by means of a standard procedure (Tassone P., et al., Tissue Antigens 51: 671 (1998)) using the four MAP-BAG3 peptides described above and are produced by at least one of the nine mother clones chosen from the following: AC-1, AC-2, AC-3, AC-4, AC-5, AC-6, AC-7, AC-8, or AC-9 (described in WO03/055908), which contain specific hybridomas for each of the four MAP-BAG3 constructs used.

According to a further embodiment, the antibodies used are monoclonal anti-BAG3 antibodies obtained from at least one of the aforesaid mother clones, and preferably at least one chosen from the following: AC-1, AC-2, AC-3, AC-4, or AC-5. More preferably, said monoclonal antibodies are obtained from at least one mother clone chosen from the following: AC-1, AC-2, and AC-3.

According to a further preferred embodiment, with the standard procedure (Ceran C, Cokol M, Cingoz S, Tasan I, Ozturk M, Yagci T. Novel anti-HER2 monoclonal antibodies: synergy and antagonism with tumor necrosis factor-α.BMC Cancer. 2012 Oct. 4; 12:450) and the immunisation of mice with a BAG3 recombinant protein, the monoclonal anti-BAG3 antibodies envisaged in the present invention are obtained from at least one of the following clones: AC-rb1, AC-rb2, AC-rb3 and AC.rb4, and/or at least one of the following subclones: AC-rb1a, AC-rb1b, AC-rb2a, AC-rb2b, AC-rb3a, AC-rb3b, AC-rb4a, and AC-rb4b. The monoclonal antibodies produced by all these clones and subclones recognise the BAG3 recombinant protein in an ELISA test. (Example 2).

Preferably, said monoclonal anti-BAG3 antibodies are those that recognise epitopes in the BAG3 protein amino acid sequence, which include at least one of the following fragments: 18-33, 385-399, 533-547 or 562-575.

A further aim of the present invention is the use of the aforesaid anti-BAG3 antibodies in the treatment of a particular pathological state which involves the activation of macrophages. Such pathological state can be chosen from:

neoplastic diseases, inflammatory diseases, immune diseases, and/or degenerative diseases.

Preferably, such neoplastic diseases may be either pancreatic tumour or bladder tumor, more preferably pancreatic tumour.

Preferably, said inflammatory diseases can be chosen from diseases related to inflammation of the skin, nerves, bones, blood vessels, and connective tissues, and more preferably, psoriasis, arthritis, neuritis, connectivitis.

Preferably, said immune diseases can be chosen from autoimmune diseases such as rheumatic diseases, connective tissue diseases, neuromuscular diseases, endocrine diseases, gastrointestinal diseases, haematologic diseases, skin diseases, and vasculitis, and more preferably, rheumatoid arthritis, multiple sclerosis, connectivitis, lupus erythematosus, endometriosis, and ulcerative colitis. Preferably, said degenerative diseases can be chosen from neurodegenerative diseases and muscular degenerative diseases, and more preferably Alzheimer's disease, Parkinson's disease, and muscular dystrophy.

According to a more preferred embodiment of the invention, the anti-BAG3 antibodies are used in the treatment of neoplastic diseases, inflammatory diseases, immune diseases, and degenerative diseases.

A further aim of the present invention is a pharmaceutical composition comprising the aforesaid anti-BAG3 antibody in association with at least one pharmaceutically acceptable excipient.

A further object of the present invention is the use of said composition as a medicament.

A preferred embodiment of the present invention is the use of the composition in the treatment of neoplastic diseases and diseases of an inflammatory, immune and/or degenerative nature.

The composition of the present invention can be formulated in a form suitable for oral administration or in a form suitable for parenteral or topical administration.

In a preferred embodiment of the present invention, said oral form can be chosen from the following: tablets, capsules, solutions, suspensions, granules, and oily capsules.

In a further preferred embodiment of the present invention, said topical form can be chosen from the following: cream, ointment, ointment, solution, suspension, eye drops, pessary, nebuliser solution, spray, powder, or gel.

In a further preferred embodiment of this invention, said parenteral form can be either an aqueous buffer solution or an oily suspension.

Said parenteral administration include administration by intramuscular, intravenous, intradermal, subcutaneous, intraperitoneal, intranodal, or intrasplenic means.

DESCRIPTION OF THE FIGURES

FIG. 1. Picture showing the reduction of tumour growth in mice treated with AC-rb2.

EXAMPLES

Example 1. Treatment of BALB/c Mice with anti-BAG3 Antibody (AC-rb2)

Nude mice (nu/nu) female BALB/c 6 weeks (Charles Rivers Wilmington, Mass., USA) were caged (3 per cage) with food and water ad libitum and kept in 12 h light/dark cycles in standard, pathogen-free conditions. The research protocol was approved by the Ethics Committee in accordance with Italian Ministry of Health official guidelines. After one week of acclimatisation, the mice were subjected to inoculation of cancer cells. 10 mice were used in total, each one individually identified. The entire experiment was conducted in laminar flow hoods and all surgical procedures were performed in strict compliance with aseptic techniques. The mice were anesthetised with 100 mg/ml of ketamine HCl and 20 mg/ml of xylazine injected intraperitoneally; they were then subjected to laparotomy and the tail of the pancreas was gently exteriorised. MIA-PaCa 2 RFP cells ($2.5 \times 10^6$) were resuspended in 40 microlitres of PBS 1× in a 1 ml syringe; using a 25 G needle, the cells were injected into the tail of the pancreas and the injection point was swabbed with sterile cotton. Once homeostasis was ascertained, the tail of the pancreas was repositioned in the abdomen and the wound closed. After two weeks, the mice were randomised into two groups: the first received an intraperitoneal injection of 100 mg/kg of mouse IgG and the second 100 mg/kg of a murine monoclonal anti-BAG3 antibody (AC-rb2). This treatment was performed twice a week in total and the mice were then anesthetised again to check the tumour area using Macro Fluo and LAS V3.7 software, by Leica Mycrosystems Ltd. In each imaging, the tumour mass was determined by quantification of the fluorescent area.

Results

Figure 2:
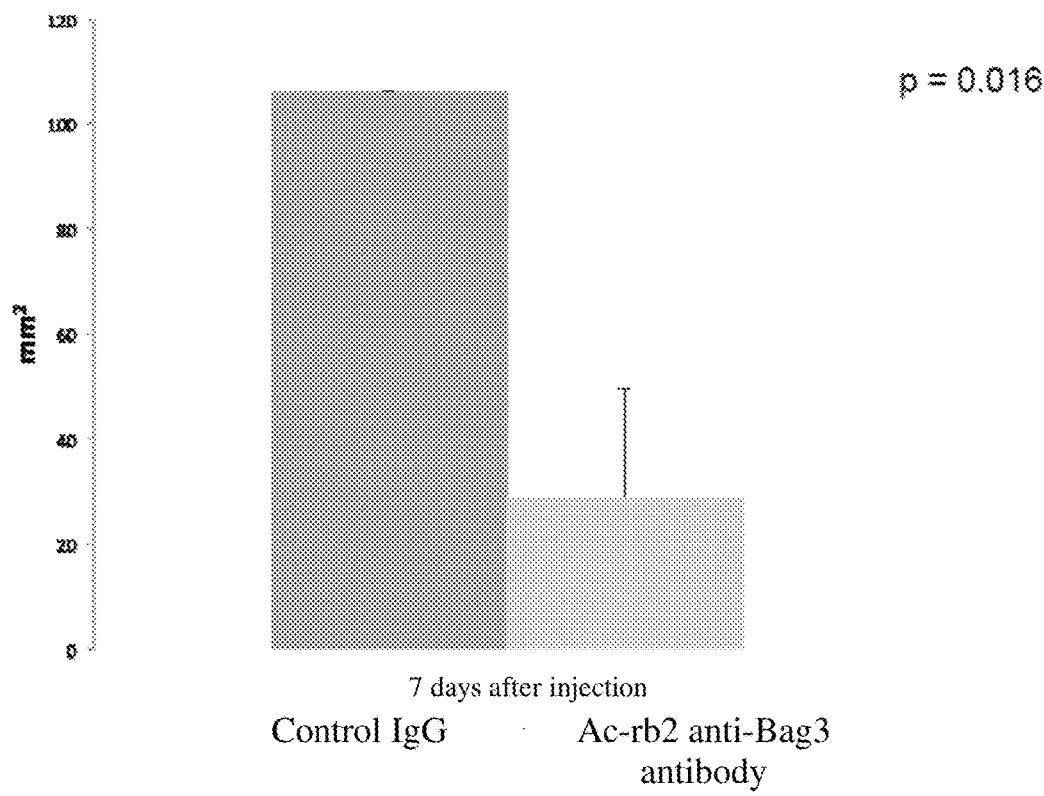
FIG. 2. Results of the reduction of tumour growth in situ.
Figure 3:
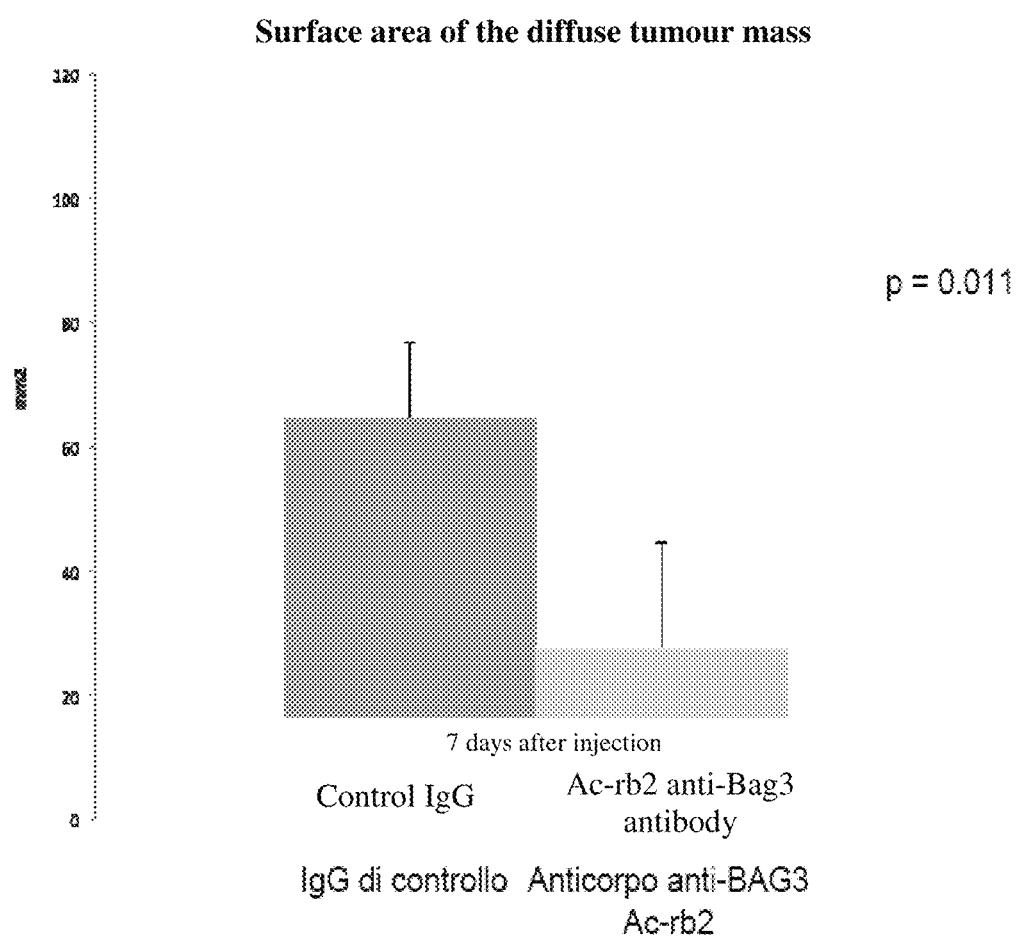
FIG. 3. Results of reduction of tumour growth in the surrounding area.

The results shown in FIGS. 1-3 demonstrate that the treatment with the Anti-BAG3 AC-rb2 antibody reduces the growth of the tumour mass by over 75% in situ and over 45% considering the area surrounding the tumour, i.e. the spread of the tumour.

Similar results were obtained with the murine monoclonal antibody AC-rb3.

Example 2. ELISA Test on the Antibodies Obtained from the Subclones AC-rb1a, AC-rb1b, AC-rb2a, AC-rb2b, AC-rb3a, AC-rb3b, AC-rb4a and AC-rb4b The NUNC Maxisorp 96-well microtiter plates were functionalised with BAG3 recombinant protein 1m/m1 in PBS 1× pH 7 (50 µl/well) and incubated for 18 hours at 4° C. The plates were then washed twice with a buffer wash (PBS 1×+0.05% Tween-20), and then kept in place for one hour at room temperature with 0.5% fish gelatin in PBS 1× (150 µl/well). Subsequently, the plates were buffer-washed twice and the supernatants of the eight subclones were diluted 1/10, 1/100, and 1/1000, in a 0.5% fish gelatin in PBS 1× and then incubated (50 µl/well) in triplicate and incubated at room temperature for 2 hours. The plates were then buffer-washed six times. To develop the signal, murine anti-IgG antibodies (H+L) (Sigma Aldrich) were used, diluted in the same buffer 1/20,000, then added to the plate (50 µl/well) and incubated at 4° C. for 30 minutes. After incubation, the plates were washed six times, then developed with TMB (50 µl/well) (eBioscience), and the reaction was stopped with sulphuric acid 4.5 M (50 µl/well). The plates were then analysed in a spectrophotometer at a wavelength of 450 nm. The results are expressed as O.D. (optical densitometry).

|  | AC-rb1 | | AC-rb2 | | AC-rb3 | | AC-rb4 | |
| --- | --- | --- | --- | --- | --- | --- | --- | --- |
| Dilution | AC-rb1a | AC-rb1b | AC-rb2a | AC-rb2b | AC-rb3a | AC-rb3b | AC-rb4a | AC-rb4b |
| 1/10 | 0.778 | 0.773 | 1.051 | 0.929 | 0.827 | 1.141 | 1.051 | 0.929 |
| 1/100 | 0.51 | 0.512 | 0.759 | 0.738 | 0.429 | 0.422 | 0.759 | 0.738 |
| 1/1000 | 0.302 | 0.31 | 0.25 | 0.232 | 0.276 | 0.207 | 0.25 | 0.232 |

The results obtained demonstrate that all the antibodies obtained by the subclones tested were able to recognise BAG3 protein.

The invention claimed is:

1. A method for treating pancreatic tumor, comprising:
   administering to a subject in need thereof an anti-BAG3 antibody produced by clone AC-1, and
   inhibiting the activity of extra-cellular BAG3 proteins on activation of macrophages,
   wherein said anti-BAG3 antibody binds to a BAG3 protein having the amino acid sequence of SEQ ID NO: 5.

2. The method according to claim 1, wherein said anti-BAG3 antibody recognizes one of the amino acid sequences of SEQ ID NOs: 1-4.

3. The method according to claim 1, wherein said anti-BAG3 antibody is produced by using an immunogen comprising four peptides having the amino acid sequences of SEQ ID NOs: 1-4.

* * * * *

SEQUENCE LISTING

<160> NUMBER OF SEQ ID NOS: 5

<210> SEQ ID NO 1
<211> LENGTH: 16
<212> TYPE: PRT
<213> ORGANISM: Homo sapiens

<400> SEQUENCE: 1

Asp Arg Asp Pro Leu Pro Pro Gly Trp Glu Ile Lys Ile Asp Pro Gln
1               5                   10                  15

<210> SEQ ID NO 2
<211> LENGTH: 15
<212> TYPE: PRT
<213> ORGANISM: Homo sapiens

<400> SEQUENCE: 2

Ser Ser Pro Lys Ser Val Ala Thr Glu Glu Arg Ala Ala Pro Ser
1               5                   10                  15

<210> SEQ ID NO 3
<211> LENGTH: 15
<212> TYPE: PRT
<213> ORGANISM: Homo sapiens

<400> SEQUENCE: 3

Asp Lys Gly Lys Lys Asn Ala Gly Asn Ala Glu Asp Pro His Thr
1               5                   10                  15

<210> SEQ ID NO 4
<211> LENGTH: 15
<212> TYPE: PRT
<213> ORGANISM: Homo sapiens

<400> SEQUENCE: 4

Asn Pro Ser Ser Met Thr Asp Thr Pro Gly Asn Pro Ala Ala Pro
1               5                   10                  15

<210> SEQ ID NO 5
<211> LENGTH: 575
<212> TYPE: PRT
<213> ORGANISM: Homo sapiens
<220> FEATURE:
<223> OTHER INFORMATION: BAG3 protein

<400> SEQUENCE: 5

Met Ser Ala Ala Thr His Ser Pro Met Met Gln Val Ala Ser Gly Asn
1               5                   10                  15

Gly Asp Arg Asp Pro Leu Pro Pro Gly Trp Glu Ile Lys Ile Asp Pro
            20                  25                  30

Gln Thr Gly Trp Pro Phe Phe Val Asp His Asn Ser Arg Thr Thr Thr
        35                  40                  45

Trp Asn Asp Pro Arg Val Pro Ser Glu Gly Pro Lys Glu Thr Pro Ser
    50                  55                  60

Ser Ala Asn Gly Pro Ser Arg Glu Gly Ser Arg Leu Pro Pro Ala Arg
65                  70                  75                  80

Glu Gly His Pro Val Tyr Pro Gln Leu Arg Pro Gly Tyr Ile Pro Ile
                85                  90                  95

Pro Val Leu His Glu Gly Ala Glu Asn Arg Gln Val His Pro Phe His
            100                 105                 110

Val Tyr Pro Gln Pro Gly Met Gln Arg Phe Arg Thr Glu Ala Ala Ala
        115                 120                 125

```
Ala Ala Pro Gln Arg Ser Gln Ser Pro Leu Arg Gly Met Pro Glu Thr
        130                 135                 140
Thr Gln Pro Asp Lys Gln Cys Gly Gln Val Ala Ala Ala Ala Ala Ala
145                 150                 155                 160
Gln Pro Pro Ala Ser His Gly Pro Glu Arg Ser Gln Ser Pro Ala Ala
                165                 170                 175
Ser Asp Cys Ser Ser Ser Ser Ser Ala Ser Leu Pro Ser Ser Gly
            180                 185                 190
Arg Ser Ser Leu Gly Ser His Gln Leu Pro Arg Gly Tyr Ile Ser Ile
        195                 200                 205
Pro Val Ile His Glu Gln Asn Val Thr Arg Pro Ala Ala Gln Pro Ser
210                 215                 220
Phe His Gln Ala Gln Lys Thr His Tyr Pro Ala Gln Gln Gly Glu Tyr
225                 230                 235                 240
Gln Thr His Gln Pro Val Tyr His Lys Ile Gln Gly Asp Asp Trp Glu
                245                 250                 255
Pro Arg Pro Leu Arg Ala Ala Ser Pro Phe Arg Ser Ser Val Gln Gly
            260                 265                 270
Ala Ser Ser Arg Glu Gly Ser Pro Ala Arg Ser Ser Thr Pro Leu His
        275                 280                 285
Ser Pro Ser Pro Ile Arg Val His Thr Val Val Asp Arg Pro Gln Gln
290                 295                 300
Pro Met Thr His Arg Glu Thr Ala Pro Val Ser Gln Pro Glu Asn Lys
305                 310                 315                 320
Pro Glu Ser Lys Pro Gly Pro Val Gly Pro Glu Leu Pro Gly His
                325                 330                 335
Ile Pro Ile Gln Val Ile Arg Lys Glu Val Asp Ser Lys Pro Val Ser
            340                 345                 350
Gln Lys Pro Pro Pro Ser Glu Lys Val Glu Val Lys Val Pro Pro
        355                 360                 365
Ala Pro Val Pro Cys Pro Pro Ser Pro Gly Pro Ser Ala Val Pro
370                 375                 380
Ser Ser Pro Lys Ser Val Ala Thr Glu Glu Arg Ala Ala Pro Ser Thr
385                 390                 395                 400
Ala Pro Ala Glu Ala Thr Pro Pro Lys Pro Gly Glu Ala Glu Ala Pro
                405                 410                 415
Pro Lys His Pro Gly Val Leu Lys Val Glu Ala Ile Leu Glu Lys Val
            420                 425                 430
Gln Gly Leu Glu Gln Ala Val Asp Asn Phe Glu Gly Lys Lys Thr Asp
        435                 440                 445
Lys Lys Tyr Leu Met Ile Glu Glu Tyr Leu Thr Lys Glu Leu Leu Ala
450                 455                 460
Leu Asp Ser Val Asp Pro Glu Gly Arg Ala Asp Val Arg Gln Ala Arg
465                 470                 475                 480
Arg Asp Gly Val Arg Lys Val Gln Thr Ile Leu Glu Lys Leu Glu Gln
                485                 490                 495
Lys Ala Ile Asp Val Pro Gly Gln Val Gln Val Tyr Glu Leu Gln Pro
            500                 505                 510
Ser Asn Leu Glu Ala Asp Gln Pro Leu Gln Ala Ile Met Glu Met Gly
        515                 520                 525
Ala Val Ala Ala Asp Lys Gly Lys Lys Asn Ala Gly Asn Ala Glu Asp
530                 535                 540
```

```
Pro His Thr Glu Thr Gln Gln Pro Glu Ala Thr Ala Ala Ala Thr Ser
545                 550                 555                 560

Asn Pro Ser Ser Met Thr Asp Thr Pro Gly Asn Pro Ala Ala Pro
                565             570                 575
```